US006682941B2

(12) United States Patent
Anderson et al.

(10) Patent No.: US 6,682,941 B2
(45) Date of Patent: Jan. 27, 2004

(54) METHOD FOR THE DETERMINATION OF THE COMPONENTS OF METAL PROTEIN COMPLEXES

(75) Inventors: Michael D. Anderson, Eden Prairie, MN (US); Mahmoud M. Abdel-Monem, Moscow, ID (US)

(73) Assignee: Zinpro Corporation, Eden Prairie, MN (US)

(*) Notice: Subject to any disclaimer, the term of this patent is extended or adjusted under 35 U.S.C. 154(b) by 329 days.

(21) Appl. No.: 09/810,265

(22) Filed: Mar. 16, 2001

(65) Prior Publication Data

US 2002/0182745 A1 Dec. 5, 2002

(51) Int. Cl.⁷ .......................... G01N 33/00; G01N 1/18
(52) U.S. Cl. .......................... 436/177; 436/178; 436/86
(58) Field of Search .......................... 436/177, 178, 436/86

(56) References Cited

U.S. PATENT DOCUMENTS 4,358,465 A * 11/1982 Brule et al. ............... 435/68.1

OTHER PUBLICATIONS

Swain et al. Isolation and Characterization of Beef Proteins That Enhance Nonheme Iron Bioavailability (poster presentation for Experimental Biology 2000 MTG, Apr. 2000).*
Vander et al. "Human Physiology: The Mechanisms of body Function", WCB/McGraw–Hill, 7th edition, pp. 570–572 (1998).*

* cited by examiner

Primary Examiner—Jill Warden
Assistant Examiner—Monique T. Cole
(74) Attorney, Agent, or Firm—McKee, Voorhees & Sease, P.L.C.

(57) ABSTRACT

A test method using ultra filtration to profile metal proteinates to evaluate their potential efficacy.

6 Claims, 1 Drawing Sheet

METHOD FOR THE DETERMINATION OF THE COMPONENTS OF METAL PROTEIN COMPLEXES

FIELD OF THE INVENTION

This invention relates to an analytical technique useful in predicting bioavailability of metal ions and amino acids from metal proteinate complexes for use in animal diet supplementation.

BACKGROUND OF THE INVENTION

The importance of the trace elements copper, iron, manganese and zinc in animal nutrition has long been recognized. The beneficial effect of iron on blood formation was recognized as early as the 17th century. In 1928, Hart, et al. provided the first conclusive evidence that copper was required for recovery from anemia in rats. Zinc was shown to be required for normal growth and health in rats in 1934 and is now considered to be essential for the health of plants, animals and humans. The essential role of manganese for the health of animals and human has been recognized since as early as 1936.

For proper health, trace elements must be provided in the diet in sufficient quantities and in a form which can be utilized by the animal. The degree to which an ingested substances is absorbed in a form that is utilizable is defined as "bioavailability". The bioavailability of nutrients for animals is summarized in a comprehensive monograph edited by Ammerman, Baker and Lewis published in 1995.

Many commercial products have been developed as additives to enhance the bioavailability of the trace elements from animal feed. The beneficial effects of these products are attributed to the association of the metal with an organic molecule, usually called a ligand. This association or bonding results in the increased availability of the metal for utilization by animals, i.e. increased bioavailability. The increased bioavailability of the trace elements in these products is a result of increased solubility, greater stability in the gut, enhanced absorption into circulation and/or improved metabolic utilization.

Different types of products that contain a trace element associated with an organic ligand are commercially available. These can be classified in different groups based on the nature of the ligand used in manufacturing the product. In one class of products, amino acids are used as the ligands that form complexes or chelates with the metal. Examples of these products are described in U.S. Pat. Nos. 3,941,818, 3,950,372, 4,067,994, 4,900,651, 4,948,594, 4,956,188, 5,061,815, 5,278,329, 5,583,243, 4,863,898 and 6,166,071. A second group of feed additives include the metal salts of short chain carboxylic acids such as propionic acid (see U.S. Pat. Nos. 5,591,878, 5,707,679, 5,795,615 and 5,846,581). A third group of trace element additives is classified by the American Feed Control Officials as Metal Proteinate and defined as "the product resulting from the chelation of a soluble salt with amino acids and/or partially hydrolyzed protein". Examples of these products are described in U.S. Pat. Nos. 3,440,054, 3,463,858, 3,775,132, 3,969,540, 4,020,158, 4,076,803, 4,103,003, 4,172,072 and 5,698,724.

Determination of the composition of the metal amino acid complexes and the metal salts of short chain carboxylic acids usually involves standard analytical methods for the determination of metals and amino acids or carboxylic acids. On the other hand, metal proteinates consist of complex mixtures of metal and a protein source. The determination of the precise composition of these proteinates is not possible because of the differences in the source and degree of hydrolysis of the protein. In some products the protein is reported to be completely hydrolyzed to the constituent amino acids by acid and enzymatic hydrolysis. Other products contain partially hydrolyzed or even un-hydrolyzed proteins. Although some methods have been reported for evaluating metal proteinates based on solubility or free metal ions activity, there is no method available for the systematic and comprehensive analysis of these products to determine if the metal and the amino acid really are bioavailable to the livestock being fed.

To evaluate the quality of commercially available metal proteinates, it is important to determine both the degree of association of the metal with the protein molecules in these products and the nature of the protein moiety. For example, a composition that has metal ions associated with folded, non-hydrolyzed protein polymer may have the same empirical formula as metal-free amino acid complex, but the bioavailability may be dramatically different.

Unfortunately, there are no current methods available for the determination of the amount of metal associated with the protein polymer molecules, or free amino acids of different molecular weights, that are usually present in these products. And, if such a technique were available it would be a useful tool in addressing effectiveness of trace element mixes to provide bioavailable supplementation of both amino acids and trace elements.

Accordingly, an objective of this invention is to provide a simple method for the analysis of metal proteinates that allows for the determination of the amount of protein present in the different molecular weight fractions and the amount of metal associated with each of these fractions. In this way, one can deduce the lowest molecular weight fractions that are associated, and from this deduce effectiveness.

Another object of the invention is to provide molecular sieve ultrafiltration data for soluble trace mineral/protein complexes, and to use the profiles of data to predict bioavailability.

An even further objective is to provide a simple and effective test which can be used to compare and predict effectiveness of trace mineral products to achieve their commercial purposes.

A still further objective is to provide a test method that is run only on the soluble portion of a trace mineral product, recognizing that the insoluble portions are not truly bioavailable.

Another objective is to provide an assay which is truly and objectively predictive of how commercially available metal proteinate complexes will perform in field trials and daily use with livestock.

The method and manner of accomplishing these and other objectives of the present invention(s) will be apparent from the detailed description of the invention(s) which follows.

SUMMARY OF THE INVENTION

Figure 1:
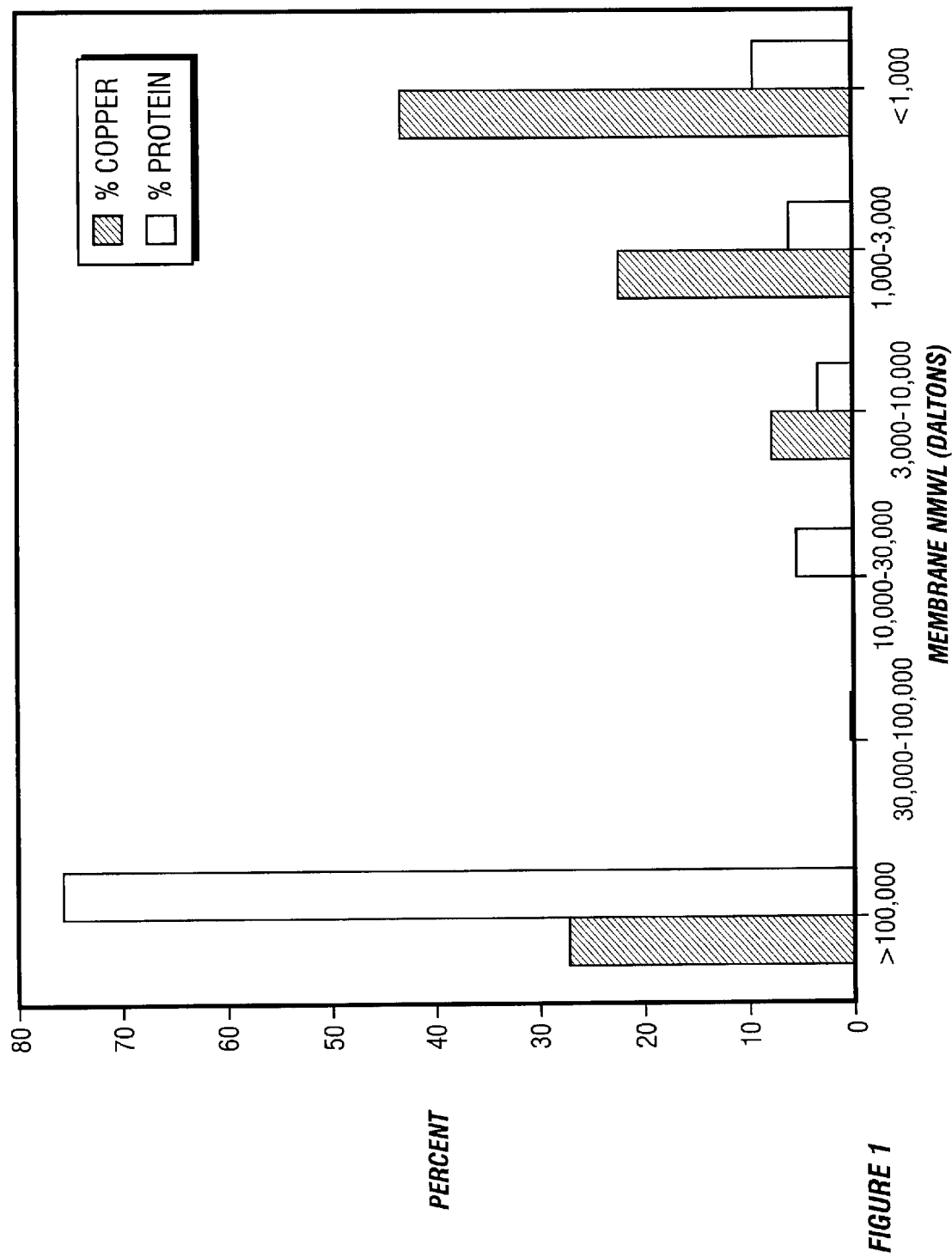
FIG. 1, shows the molecular weight and copper distribution profile for the sample tested in example 2.

A simple and effective method for the systematic and comprehensive analysis and profiling of the composition of metal proteinates is provided. A sample of the metal proteinate is extracted in water in some cases or in some cases mild acid to simulate the gut pH. The protein and metal content of the extract are determined using an appropriate and known quantitative procedure. Part of the extract is then filtered through a series of ultrafiltration membranes. The ultrafiltrates are analyzed each for the metal and protein contents. The amount of protein and metal present in each fraction with a known range of molecular weight (because one knows the weight which will pass through the sieve) is calculated. This is most conveniently expressed as percent of the total amount present in the product. The more that is present in the smaller molecular weight fractions the more likely it will be bioavailable.

DETAILED DESCRIPTION OF THE PREFERRED EMBODIMENT

In this invention, a method is provided to separate the soluble metal proteinate contents of a sample into fractions based on the molecular weight of the proteinate. The amount of metal and protein in each fraction are then determined. This invention allows for the determination of the degree of hydrolysis of the protein source in the metal proteinate. Subjecting successive soluble samples of metal proteinates of unknown composition to this simple procedure allows for establishing a profile of protein and associated metal in each of the molecular weight fractions which can then be used to predict efficacy.

In a first step an accurately weighed sample of the metal proteinate is mixed with water and incubated at from 25° C. to 50° C., preferably 37° C. with occasional shaking for from 30–60 minutes. The mixture is then transferred into a volumetric flask and completed to volume. Accurately measured portions of the extract are then subjected to a series of ultrafiltration steps using various size filters. The protein and metal contents of the original extract and each of the ultrafiltrates are determined by using the appropriate standard quantitative methods.

Ultrafiltration, also known as molecular filtration is a technique used to segregate substances according to molecular weight and molecule size. A solution containing molecules of different sizes is passed through a series of semi-permeable membranes. These membranes have pore diameters ranging from 1 to 1,000 Angstroms and under normal operating pressures will separate molecules ranging in molecular weight from 100 to 1,000,000. Each ultrafiltration membrane is characterized by its normal molecular weight limit (NMWL). NMWL is expressed in kilo Daltons and abbreviated as Kd or K. Molecules will pass through the membrane and if found in the ultrafiltrate are therefore known to have a molecular weight less than the sieve rating. Molecules with molecular weight larger than the nominal molecular weight limit of the membrane or sieve are retained on the filter. Usually, an ultrafiltration membrane with a stated NMWL will retain at least 90% of a globular solute of that molecular weight in Daltons.

Several technologies are commercially available to separate molecules by ultrafiltration. The most common of these techniques is the pressurized stirred cell system. This system utilizes a closed container in which the ultrafiltration membrane is placed horizontally. The sample is introduced in the cell and the system is pressurized to force water and small molecules through the membrane. The contents of the cell are continuously stirred to prevent the accumulation of retained molecules on the membrane. Another commercially available technology is Centrifuge Separation, which utilizes centrifugal force to push the ultrafiltrate through the membrane. Other systems are tangential flow and Vertical Filtration technologies. All can be used in this invention.

While the nominal molecular weight limits (NMWL) of membranes that are used can vary, it is preferred to use ultrafiltration membranes of the following NMWL: 500,000, 100,000, 30,000, 10,000, 3,000, and 1,000. This allows the collection of fractions containing molecules of the following range of molecular weights: 100,000–500,000, 30,000–100,000, 10,000–30,000, 3,000–10,000, 1,000–3,000 and less than 1,000. As a profiling trend that is predictive, the more metal and protein/amino acids are present together in the lower molecular weight fractions, the more effective the trace mineral mix will be when fed to animals. It is preferred that 90% of the metal and the protein/amino acids are present together in the less than 1,000 molecular weight fraction.

The following examples are offered to illustrate the applications of this invention to the analysis of commercial metal proteinate products. The results of analysis of products containing metal complexes of amino acids produced by the complete hydrolysis of a protein source are also presented to demonstrate the ability of the invention to differentiate commercial products.

It goes without saying that modifications to the precise conditions shown can be made and still come within the scope of the invention(s).

EXAMPLE 1

Analysis of a Zinc Proteinate Sample

A sample of a commercially available zinc proteinate was accurately weighed (51.233 g) and transferred into a 600-ml beaker. A 300-ml aliquot of water was added and the mixture was magnetically stirred for 15 minutes at room temperature. The extract contained carrier(s) that formed a gelatinous materials on mixing with water. The gelatinous materials were removed by quantitative vacuum filtration through a course filter paper. The filtrate was transferred into a stirred ultrafiltration cell (Amicon 8400) fitted with a polysulfone membrane with a nominal molecular weight limit of 500,000 Daltons (Millipore ZM500, Dia: 76 mm). The sample was filtered under nitrogen at 50 psi. The ultrafiltrate was collected in a 500-ml volumetric flask. The cell and filter were washed four times by placing 30-ml of distilled water in the stirred cell and passing the wash through the membrane under 50 psi of nitrogen. The washings were collected in the same 500-ml volumetric flask as the filtrate. The ultrafiltrate was completed to volume with distilled water and marked as "Stock Solution A". The protein and zinc content of "Stock Solution A" were determined (see Table 1).

A 75-ml portion of "Stock Solution A" was accurately measured into a stirred ultrafiltration cell (Amicon 8200) fitted with a regenerated cellulose membrane with a nominal molecular weight limit of 100,000 Daltons (Millipore YM100, Dia: 63.5-mm).

The sample was filtered under nitrogen at 50 psi. The ultrafiltrate was collected in a 100-ml volumetric flask. The cell and filter were washed twice by placing 5-ml of distilled water in the stirred cell and passing the wash through the membrane under 50 psi of nitrogen. The washings were collected in the same 100-ml volumetric flask as the filtrate. The ultrafiltrate was completed to volume with distilled water and marked "Ultrafiltrate 100K". The protein and zinc content of "Ultrafiltrate 100K" were determined (see table 1).

The ultrafiltration was repeated by using a regenerated cellulose membranes with nominal molecular weight limits of 30,000, 10,000, 3,000, and 1,000 Daltons (Millipore YM30, 10, 3 and 1 respectively). The ultrafiltrates after each operation was marked "Ultrafiltrate 30K", "Ultrafiltrate 10K", "Ultrafiltrate 3K", and "Ultrafiltrate 1K", respectively.

The protein contents of "Stock Solution A" and the ultrafiltrates were determined by the Modified Lowery Protein Method using a commercially available Protein Assay Kit (P-5656, Sigma Diagnostics).

The zinc contents of "Stock Solution A" and the ultrafiltrates were determined by AOAC Official Method 944.09.

The results of the determination of protein and zinc content of "Stock Solution A" and the ultrafiltrates are reported in TABLE 1. The profile shows that the protein in this sample is present in a variety of molecules of different molecular weights. However, it appears that the majority of zinc is present in the less than 1000 Dalton fraction which contain only a small amount of protein indicating that it is in the form of inorganic salts.

TABLE 1

| Sample identification | Protein Content* | Zinc Content* |
| --- | --- | --- |
| Stock Solution A | 20.52 | 13.18 |
| Ultrafiltrate 100K | 5.88 | 13.18 |
| Ultrafiltrate 30K | 5.77 | 12.44 |
| Ultrafiltrate 10K | 3.96 | 11.64 |
| Ultrafiltrate 3K | 3.28 | 11.24 |
| Ultrafiltrate 1K | 1.88 | 10.08 |

*Expressed as g/100 g of Original Product.

The protein and zinc content of each of the nominal molecular weight fractions were calculated and are reported in TABLE 2. Over 70% of the protein in the sample was found in the >100,000 nominal molecular weight fraction. Interestingly, this fraction did not contain measurable amounts of zinc. The other fractions contained only small amounts of zinc. More than 75% of the zinc was found in the <1000 nominal molecular weight fraction. This fraction contained less than 10% of the protein present in the sample.

TABLE 2

| Nominal Molecular Weight Fraction | Protein Content* | Zinc Content* |
| --- | --- | --- |
| >100,000 | 14.64 | 0.00 |
| 30,000–100,000 | 0.11 | 0.74 |
| 10,000–30,000 | 1.82 | 0.80 |
| 3,000–10,000 | 0.67 | 0.40 |
| 1,000–3,000 | 1.41 | 1.16 |
| <1000 | 1.88 | 10.08 |

*Expressed as g/100 g of Original Product.

Table 3 reports the % of protein and zinc in the sample that were present in each of the fractions.

TABLE 3

| Nominal Molecular Weight Fraction | % of Protein* | % of Zinc |
| --- | --- | --- |
| >100,000 | 71.34 | 0.00 |
| 30,000–100,000 | 0.53 | 5.61 |
| 10,000–30,000 | 8.86 | 6.07 |
| 3,000–10,000 | 3.29 | 3.03 |
| 1,000–3,000 | 6.85 | 8.80 |
| <1000 | 9.14 | 76.48 |

*Expressed as % of Amount found in the Product.

Since so much of the protein is larger molecular weight fractions, the amino acid moieties are likely not very available and the efficacy of the product would not be expected to be very good.

EXAMPLE 2

Analysis of a Copper Proteinate Sample

A sample of a commercially available copper proteinate was accurately weighed (50.147 g) and transferred into a 600-ml beaker. A 300-ml of water was added and the mixture was magnetically stirred for 15 minutes at room temperature. The extract contained carrier(s) that formed gelatinous materials on mixing with water. The gelatinous materials were removed by quantitative vacuum filtration through a course filter paper. The filtrate was transferred into a stirred ultrafiltration cell (Amicon 8400) fitted with a polysulfone membrane with a nominal molecular weight limit of 500,000 Daltons (Millipore ZM500, Dia: 76 mm). The sample was filtered under nitrogen at 50 psi. The ultrafiltrate was collected in a 500-ml volumetric flask. The cell and filter were washed four times by placing 30-ml of distilled water in the stirred cell and passing the wash through the membrane under 50 psi of nitrogen. The washings were collected in the same 500-ml volumetric flask as the filtrate. The ultrafiltrate was completed to volume with distilled water and marked as "Stock Solution A". The protein and copper content of "Stock Solution A" were determined.

A 50-ml portion of "Stock Solution A" was accurately measured into a stirred ultrafiltration cell (Amicon 8200) fitted with a regenerated cellulose membrane with a nominal molecular weight limit of 100,000 Daltons (Millipore YM100, Dia: 63.5 mm). The sample was filtered under nitrogen at 50 psi. The ultrafiltrate was collected in a 100-ml volumetric flask. The cell and filter was washed four times by placing 5-ml of distilled water in the stirred cell and passing the wash through the membrane under 50 psi of nitrogen. The washings were collected in the same 100-ml volumetric flask as the filtrate. The ultrafiltrate was completed to volume with distilled water and mark "Ultrafiltrate 100 K". The protein and copper content of "Ultrafiltrate 100K" were determined.

The ultrafiltration was repeated by using regenerated cellulose membranes with nominal molecular weight limits of 30,000, 10,000, 3,000, and 1,000 Daltons (Millipore YM30, 10, 3 and 1 respectively). The ultrafiltrates after each operation was marked "Ultrafiltrate 30K", "Ultrafiltrate 10K", "Ultrafiltrate 3K", and "Ultrafiltrate 1K", respectively.

The protein contents of "Stock Solution A" and the ultrafiltrates were determined by the Modified Lowery Protein Method using a Protein Assay Kit (P-5656, Sigma Diagnostics).

The copper contents of "Stock Solution A" and the ultrafiltrates were determined by an Iodometric titration.

The results of the determination of protein and copper content of "Stock Solution A" and the ultrafiltrates are reported in TABLE 4. It appears that the protein in this sample is present in a variety of molecules of different molecular weights. However, it appears that a large portion of copper is present in the form of low molecular weight compounds primarily in the form of inorganic compounds.

TABLE 4

| Sample Identification | Protein Content* | Copper Content* |
|---|---|---|
| Stock Solution A | 29.23 | 8.79 |
| Ultrafiltrate 100 | 7.10 | 6.395 |
| Ultrafiltrate 30 | 6.97 | 6.395 |
| Ultrafiltrate 10 | 5.38 | 6.395 |
| Ultrafiltrate 3 | 4.41 | 5.728 |
| Ultrafiltrate 1 | 2.68 | 3.779 |

*Expressed as g/100 g of Original Product.

The protein and copper content of each of the nominal molecular weight fractions were calculated and are reported in TABLE 5. TABLE 6 reports the % of protein and copper in the sample that were present in each of the fractions. The same results are presented graphically in FIG. 1.

TABLE 5

| Nominal Molecular Weight Fraction | Protein Content* | Copper Content* |
|---|---|---|
| >100,000 | 22.13 | 2.40 |
| 30,000–100,000 | 0.13 | 0.00 |
| 10,000–30,000 | 1.59 | 0.00 |
| 3,000–10,000 | 0.97 | 0.67 |
| 1,000–3,000 | 1.73 | 1.95 |
| <1000 | 2.68 | 3.78 |

*Expressed as g/100 g of Original Product.

TABLE 6

| Nominal Molecular Weight Fraction | % Protein* | % Copper |
|---|---|---|
| >100,000 | 75.70 | 27.31 |
| 30,000–100,000 | 0.46 | 0.00 |
| 10,000–30,000 | 5.43 | 0.00 |
| 3,000–10,000 | 3.33 | 7.59 |
| 1,000–3,000 | 5.92 | 22.17 |
| <1000 | 9.17 | 42.99 |

Over 75% of the protein in the sample was present in the fraction >100,000. Only 27% of copper was present in this sample. Nearly 43.31% of copper was present in the fraction <1000 but only 9.17% of protein was present in this fraction.

EXAMPLE 3

Analysis of a Zinc Amino Acid Complexes Sample

A sample of a commercially available zinc amino acid complexes was accurately weighed (44.910 g) and transferred into a 600-ml beaker. A 300-ml aliquot of water was added and the mixture was magnetically stirred for 15 minutes at room temperature. The extract contained a large amount of carrier(s) that was removed by quantitative vacuum filtration through a coarse filter paper. The filtrate was transferred into a stirred ultrafiltration cell (Amicon 8400) fitted with a polysulfone membrane with a nominal molecular weight limit of 500,000 Daltons (Millipore ZM500, Dia: 76 mm). The sample was filtered under nitrogene at 50 psi. The ultrafiltrate was collected in a 500-ml volumetric flask. The cell and filter were washed four times by placing 30-ml of distilled water in the stirred cell and passing the wash through the membrane under 50 psi of nitrogen. The washings were collected in the same 500-ml volumetric flask as the filtrate. The ultrafiltrate was completed to volume with distilled water and marked as "Stock Solution A". The protein, zinc and amino acid contents of "Stock Solution A" were determined (see Table 7).

A 75-ml portion of "Stock Solution A" was accurately measured into a stirred ultrafiltration cell (Amicon 8200) fitted with a regenerated cellulose membrane with a nominal molecular weight limit of 100,000 Daltons (Millipore YM100, Dia: 63.5-mm).

The sample was filtered under nitrogen at 50 psi. The ultrafiltrate was collected in a 100-ml volumetric flask. The cell and filter were washed twice by placing 5-ml of distilled water in the stirred cell and passing the wash through the membrane under 50 psi of nitrogen. The washings were collected in the same 100-ml volumetric flask as the filtrate. The ultrafiltrate was completed to volume with distilled water and marked "Ultrafiltrate 100K". The protein and zinc content of "Ultrafiltrate 100K" were determined (see table 7).

The ultrafiltration was repeated by using a regenerated cellulose membranes with nominal molecular weight limits of 30,000, 10,000, 3,000, and 1,000 Daltons (Millipore YM30, 10, 3 and 1 respectively). The ultrafiltrates after each operation was marked "Ultrafiltrate 30K", "Ultrafiltrate 10K", "Ultrafiltrate 3K", and "Ultrafiltrate 1K", respectively.

The protein contents of "Stock Solution A" and the ultrafiltrates were determined by the Modified Lowery Protein Method using a commercially available Protein Assay Kit (P-5656, Sigma Diagnostics).

The zinc contents of "Stock Solution A" and the ultrafiltrates were determined by AOAC Official Method 944.09.

The amino acid contents of "Stock Solution A" and the ultrafiltrates were determined by the method described by S. Moore published in the Journal of Biological Chemistry, volume 243, pages 6281–6283 (1968).

The results of the determination of protein, amino acids and zinc content of "Stock Solution A" and the ultrafiltrates are reported in TABLE 7. The profile shows that the protein, amino acids and zinc are present in the form of low molecular weight compounds thus indicating that it is bioavailable.

TABLE 7

| Sample identification | Protein Content* | Zinc Content* | Amino Acids* |
|---|---|---|---|
| Stock Solution A | 2.560 | 10.46 | 15.840 |
| Ultrafiltrate 100K | 2.480 | 10.41 | 15.830 |
| Ultrafiltrate 30K | 2.475 | 10.39 | 15.825 |
| Ultrafiltrate 10K | 2.473 | 10.37 | 15.700 |
| Ultrafiltrate 3K | 2.470 | 10.31 | 15.600 |
| Ultrafiltrate 1K | 2.460 | 10.15 | 15.420 |

*Expressed as g/100 g of Original Product.

The protein, amino acids and zinc content of each of the nominal molecular weight fractions were calculated and are reported in TABLE 8. Over 95% of the protein, amino acids and zinc were present in the ultrafiltrate fraction of less than 1000 Daltons.

TABLE 8

| Nominal Molecular Weight Fraction | Protein Content* | Zinc Content* | Amino Acid Content* |
|---|---|---|---|
| 100,000–500,000 | 0.08 | 0.05 | 0.01 |
| 30,000–100,000 | 0.005 | 0.02 | 0.005 |
| 10,000–30,000 | 0.001 | 0.02 | 0.125 |
| 3,000–10,000 | 0.003 | 0.06 | 0.100 |

TABLE 8-continued

| Nominal Molecular Weight Fraction | Protein Content* | Zinc Content* | Amino Acid Content* |
|---|---|---|---|
| 1,000–3,000 | 0.010 | 0.16 | 0.180 |
| <1000 | 2.46 | 10.15 | 15.42 |

*Expressed as g/100 g of Original Product.

Table 9 reports the % of protein and zinc in the sample that were present in each of the fractions.

TABLE 9

| Nominal Molecular Weight Fraction | % of Protein* | % of Zinc | % of Amino Acids |
|---|---|---|---|
| 100,000–500,000 | 3.13 | 0.48 | 0.06 |
| 30,000–100,000 | 0.20 | 0.19 | 0.03 |
| 10,000–30,000 | 0.08 | 0.19 | 0.79 |
| 3,000–10,000 | .12 | 0.57 | 0.63 |
| 1,000–3,000 | 0.39 | 1.53 | 1.14 |
| <1000 | 96.09 | 97.04 | 97.35 |

*Expressed as % of Amount found in the Product.

Since the majority of the metal, amino acid and protein are present in the same low molecular weight fraction, the efficacy of the product would be expected to be very good.

EXAMPLE 4

Effects of Metal Amino Acid Complexes Compared to Metal Proteinates on Egg Production and Egg Quality of DeKalb Delta Layers Between 54 and 70 Weeks of Age Numerous products are used to improve production and egg shell strength of laying hens. Many of these products are especially touted to be effective during heat stress. Organic trace mineral sources (e.g. Metal Amino Acid Complexes and Metal Proteinates) are being marketed to improve egg shell strength, especially during the summer and in layers in the later phases of production. A total of 432 DeKalb Delta laying hens were used to evaluate the efficacy of Metal Amino Acid Complexes compared to Metal Proteinates on egg production and egg quality. Hens were randomly assigned to one of three dietary treatments: Control, Control plus Metal Amino Acid Complexes (Complexes, Control plus 7.5 ppm added Zn, 4.5 ppm added Mn, and 1.0 ppm added Cu) and Control plus Metal Proteinates (Proteinates; Control plus 7.5 ppm added Zn, 4.5 ppm added Mn, and 1.0 ppm added Cu). The control diet contained 182 ppm Zn, 111 ppm Mn and 13 ppm Cu. Diets were fed from 54 to 70 weeks of age. All diets were formulated to contain equal amounts of Na, Cl, Ca and P. Metal Amino Acid Complexes (7.5 ppm added Zn, 4.5 ppm added Mn, and 1.0 ppm added Cu) improve (P<0.05) hen day egg production, egg weight, egg mass, and feed conversion ratio (Table 10) compared to equal levels of added Metal Proteinates in DeKalb laying hens from 54 to 70 weeks of age.

TABLE 10

Effect of Metal Amino Acid Complexes Compared to Metal Proteinates for Laying Hens

|  | Control | Complexes[a] | Proteinates[b] |
|---|---|---|---|
| Hen day egg production, % | 78.22[y] | 81.57[z] | 76.95[y] |
| Egg weight, g | 64.74[y] | 66.39[z] | 63.81[y] |
| Egg mass, g | 50.67[y] | 54.18[z] | 49.11[y] |
| Feed/egg ratio | 2.01[yz] | 1.96[z] | 2.08[y] |

[a]Control plus 7.5 ppm added Zn, 4.5 ppm added Mn and 1.0 ppm added Cu from Metal Amino Acid Complexes
[b]Control plus 7.5 ppm added Zn, 4.5 ppm added Mn and 1.0 ppm added Cu from Metal Proteinates
[y,z]Within a row, means lacking a common superscript letter differ (P < 0.05)

The proteinate of this example is the same commercially available sample tested in example 1, the amino acid complexes is the same commercially available sample tested in example 3, and the test confirms the validity of the test and predictive profile of this invention.

From the above examples and description of the preferred embodiment, it can be seen that the invention accomplishes its stated objectives.

What is claimed is:

1. A method of determining metal protein complex efficacy in providing bioavailable metal and amino acid sources, comprising:

preparing a sample of dissolved metal proteinate;

ultrafiltering separate portions of the dissolved metal proteinate in separate steps through a series of ultrafiltration membranes each of progressively smaller molecular weight range to provide an ultrafiltrate;

determining the metal content and the protein content of each separate ultrafiltrate to provide a profile;

assessing the efficacy of the metal protein complex based upon the profile of the ultrafiltrate portions.

2. The method of claim 1 wherein the ultrafilters used in the ultrafiltration steps have nominal molecular weight limits of 500,000, 100,000, 30,000, 10,000, 3,000 and 1,000.

3. The method of claim 1 wherein the sample is dissolved in water at a temperature of from 25° C. to 50° C.

4. The method of claim 3 wherein the sample is dissolved at 37° C.

5. The method of claim 1 wherein the sample is dissolved in water adjusted to pH within the range of 2.5 to 3.0.

6. The method of claim 1 wherein the ultrafilters used in the ultrafiltration steps include an ultrafilter with a nominal molecular weight limit of 1000.

* * * * *